United States Patent
Shafique et al.

(10) Patent No.: US 11,712,193 B2
(45) Date of Patent: Aug. 1, 2023

(54) RELIABLE SEIZURE DETECTION WITH A PARALLELIZABLE, MULTI-TRAJECTORY ESTIMATE OF LYAPUNOV EXPONENTS

(71) Applicants: Arizona Board of Regents on behalf of Arizona State University, Scottsdale, AZ (US); DIGNITY HEALTH, San Francisco, CA (US)

(72) Inventors: Ashfaque Shafique, Chandler, AZ (US); David Treiman, Phoenix, AZ (US); Konstantinos Tsakalis, Chandler, AZ (US)

(73) Assignees: Arizona Board of Regents on behalf of Arizona State University, Scottsdale, AZ (US); Dignity Health, San Francisco, CA (US)

(*) Notice: Subject to any disclaimer, the term of this patent is extended or adjusted under 35 U.S.C. 154(b) by 748 days.

(21) Appl. No.: 16/326,259

(22) PCT Filed: Aug. 17, 2017

(86) PCT No.: PCT/US2017/047303
§ 371 (c)(1),
(2) Date: Feb. 18, 2019

(87) PCT Pub. No.: WO2018/035299
PCT Pub. Date: Feb. 22, 2018

(65) Prior Publication Data
US 2019/0209072 A1  Jul. 11, 2019

Related U.S. Application Data

(60) Provisional application No. 62/376,330, filed on Aug. 17, 2016.

(51) Int. Cl.
*A61B 5/291* (2021.01)
*A61B 5/316* (2021.01)
(Continued)

(52) U.S. Cl.
CPC ............ *A61B 5/4094* (2013.01); *A61B 5/291* (2021.01); *A61B 5/316* (2021.01); *A61B 5/369* (2021.01);
(Continued)

(58) Field of Classification Search
CPC ..... A61B 5/742; A61B 5/7282; A61B 5/7235; A61B 5/6803; A61B 5/316; A61B 5/291;
(Continued)

(56) References Cited

U.S. PATENT DOCUMENTS 7,461,045 B1 * 12/2008 Chaovalitwongse .. A61B 5/369
706/52
8,197,395 B2   6/2012 Jassemidis
(Continued)

FOREIGN PATENT DOCUMENTS

WO   2006019822   2/2006
WO   2016/029293  3/2016

OTHER PUBLICATIONS

Paivinen et al. "Epileptic seizure detection: A nonlinear viewpoint", Computer Methods and Programs in Biomedicine (2005) 79, 151—159 (Year: 2005).*
(Continued)

*Primary Examiner* — Navin Natnithithadha
(74) *Attorney, Agent, or Firm* — Quarles & Brady, LLP

(57) ABSTRACT

Systems and methods for tracking EEG data and providing enhanced seizure detection and prediction are disclosed. The systems and methods use input sensors for receiving and collecting data from a plurality of EEG channels in association with a subject and processing said data to calculate and average Lyapunov exponents for a composite EEG data set. The systems and methods convert the average Lyapunov exponents into graphical representations that are displayed against a time axis. The graphical output adjusts in real-time
(Continued)

according to the input data obtained from EEG channels. The systems and methods utilize pattern recognition to output alarms based upon input data and recommend diagnoses related to seizures.

8 Claims, 9 Drawing Sheets

(51) Int. Cl.
  A61B 5/369 (2021.01)
  A61B 5/00 (2006.01)
(52) U.S. Cl.
  CPC .......... *A61B 5/6803* (2013.01); *A61B 5/7235* (2013.01); *A61B 5/7282* (2013.01); *A61B 5/742* (2013.01)
(58) Field of Classification Search
  CPC ......... A61B 5/372; A61B 5/367; A61B 5/369; A61B 5/4076; A61B 5/4094
  See application file for complete search history.

(56) References Cited

U.S. PATENT DOCUMENTS

| | | | | |
|---|---|---|---|---|
| 10,098,582 | B1* | 10/2018 | McNair | G16H 40/67 |
| 2007/0174377 | A2 | 7/2007 | Shiomi et al. | |
| 2007/0213786 | A1 | 9/2007 | Sackellares et al. | |
| 2010/0286747 | A1* | 11/2010 | Sabesan | A61B 5/4094 607/45 |
| 2013/0035579 | A1 | 2/2013 | Le et al. | |

OTHER PUBLICATIONS

Grush, Loren, "Those 'mind reading' EEG headsets definitely can't read your thoughts", The Verge, Jan. 12, 2016 (Year: 2016).*
Esteller et al. "Line length: An efficient feature for seizure onset detection"; 2001 Proceedings of the 23rd Annual EMBS International Conference, October 25-28, Istanbul, Turkey; 1707-1710 (Year: 2001).*
Abarbanel Henry DI, et al. Analysis of observed chaotic data. Physics Today, 49:86, 1996.
Centers for Disease Control and Prevention. Epilepsy fast facts, 2016.
Citizens for Research in Epilepsy. Epilepsy facts, 2016.
Gabor, AJ et al. Automated seizure detection using a self-organizing neural network. Electroencephalography and clinical Neurophysiology, 99(3):257-266, 1996.
Gardner Andrew B et al. One-class novelty detection for seizure analysis from intracranial eeg. The Journal of Machine Learning Research, 7:1025-1044, 2006.
Grassberger Peter et al. Characterization of strange attractors. Physical review letters, 50(5):346-349, 1983.
Grassberger Peter et al. Nonlinear time sequence analysis. International Journal of Bifurcation and Chaos, 1(03):521-547, 1991.
Iasemidis, LD, et al The evolution with time of the spatial distribution of the largest lyapunov exponent on the human epileptic cortex. Measuring chaos in the human brain, pp. 49-82, 1991.
Iasemidis, LD, et al. Epileptic seizure prediction and control. Biomedical Engineering, IEEE Transactions on, 50(5):549-558, 2003.
Iasemidis, LD, et al. Measurement and quantification of spatiotemporal dynamics of human epileptic seizures. Nonlinear biomedical signal processing, 2:294-318, 2000.
Iasemidis, LD, et al. Nonlinear dynamics of electro-corticographic data. J. Clin. Neurophysiol, 5:339, 1988.

Kantz, H. A robust method to estimate the maximal lyapunov exponent of a time series. Physics letters A, 185(1):77-87, 1994.
Kramer, U., et al. A novel portable seizure detection alarm system: preliminary results. Journal of Clinical Neurophysiology, 28(1):36-38, 2011.
Kwan, P., et al. Early identification of refractory epilepsy. New England Journal of Medicine, 342(5):314-319, 2000.
Lehnertz, K., et al. Its possible use for interictal focus localization, seizure anticipation, and prevention: Nonlinear eeg analysis in epilepsy. Journal of Clinical Neurophysiology, 18(3):209-222, 2001.
Mormann, F., et al. Epileptic seizures are preceded by a decrease in synchronization. Epilepsy Research, 53(3):173 185, 2003.
Packard, NH, et al. Geometry from a time series. Physical Review Letters, 45:712-716, 1980.
Pardalos, PM, et al. Seizure warning algorithm based on spatiotemporal dynamics of intracranial eeg. Mathematical Programming, 101(2):365-385, 2004.
Qu, H., et al. A patient-specific algorithm for the detection of seizure onset in long-term eeg monitoring: possible use as a warning device. Biomedical Engineering, IEEE Transactions on, 44(2):115 122, 1997.
Rosenstein, M. T., et al. A practical method for calculating largest lyapunov exponents from small data sets. Physica D: Nonlinear Phenomena, 65(1):117-134, 1993.
Sabesan, S. Spatiotemporal brain dynamics in epilepsy: application to seizure prediction and focus localization. ProQuest, 2008.
Takens, F. Detecting strange attractors in turbulence. In Dynamical systems and turbulence, Warwick 1980, pp. 366-381. Springer, 1981.
Tzallas, A. T., et al. Epileptic seizure detection in eegs using time-frequency analysis. Information Technology in Biomedicine, IEEE Transactions on, 13(5):703-710, 2009.
Wolf, A., et al. Determining lyapunov exponents from a time series. Physica D: Nonlinear Phenomena, 16(3):285-317, 1985.
Gao, J. et al., "Fast monitoring of epileptic seizures using recurrence time statistics of electroencephalography", Frontiers in Computational Neuroscience, Oct. 2013, vol. 7, Article 122, 8 pages DOI:10.3389/fncom.2013.00122.
Kowalik, Z. et al., "Local Lyapunov exponents detect epileptic zones in spike-less interictal MEG recordings", Clinical Neurophysiology, Jan. 2001 [available online Dec. 2000], vol. 112, No. 1, pp. 60-67 DOI:10.1016/S1388-2457(00)00465-X.
Lai, Y .et al., "Controlled test for predictive power of Lyapunov exponents: their inability to predict epileptic seizures", Chaos, Sep. 2004, vol. 14, No. 3, pp. 630-642 DOI:10.1063/1.1777831.
Lehnertz, K., "Non-linear time series analysis of intracranial EEG recordings in patients with epilepsy—an overview", International Journal of Psychophysiology, Oct. 1999, vol. 34, No. 1, pp. 45-52 DOI:10.1016/S0167-8760(99)00043-4.
Lehnertz, K., "Epilepsy and Nonlinear Dynamics", Journal of Biological Physics, Aug. 2008 [available online Jul. 2008], vol. 34, No. 3-4, pp. 253-266 DOI:10.1007/s10867-008-9090-3.
International Search Report and Written Opinion for International Patent Application No. PCT/US2017/047303 with a dated Oct. 27, 2017.
Fiasche et al., "Integrating Neural Networks and Chaotic Measurements for Modelling Epileptic Brain," Artificial Neural Networks and Machine Learning—ICANN 2012, 22nd International Conference on Artificial Neural Networks, Lausanne, Switzerland, Sep. 11-14, 2012, Proceedings, Part I, Lecture Notes in Computer Science, vol. 7552. Springer, Berlin, Heidelberg. https://doi.org/10.1007/978-3-642-33269-2_82, pp. 653-660.
European Patent Office. Extended European Search Report for application 17842100.4. dated Jun. 30, 2020. 12 pages.
Response to European Patent Office communication issued pursuant to Rules 70(2) and 70a(2) EPC for application 17842100.4. Response dated Jan. 27, 2021. 3 pages.

* cited by examiner

RELIABLE SEIZURE DETECTION WITH A PARALLELIZABLE, MULTI-TRAJECTORY ESTIMATE OF LYAPUNOV EXPONENTS

CROSS-REFERENCE TO RELATED APPLICATION

This application represents the national stage entry of PCT International Application No. PCT/US2017/047303, filed on Aug. 17, 2017, and, claims priority to U.S. Provisional Patent Application No. 62/376,330 entitled "RELIABLE SEIZURE DETECTION WITH A PARALLELIZABLE, MULTI-TRAJECTORY ESTIMATE OF LYAPUNOV EXPONENTS" and filed on Aug. 17, 2016.

FIELD OF THE INVENTION

This disclosure relates to systems, methods, and devices that utilize data associated with an individual or subject's EEG recordings to track and detect seizures.

STATEMENT REGARDING FEDERALLY SPONSORED RESEARCH

This invention was made with government support under ECCS-1102390 awarded by the National Science Foundation. The government has certain rights in the invention.

BACKGROUND OF THE INVENTION

Epilepsy is a neurological disorder characterized by seizures, which are recurrent perturbations of normal brain function. It is the third most common neurological disorder after stroke and Alzheimer's disease, and affects at least 65 million people world-wide with an incidence rate of 200,000 people per year. Of the 2.2 million troops returning from Iraq and Afghanistan, 100,000 are estimated to develop post-traumatic epilepsy (PTE). The Center for Disease Control estimates 5.1 million adults and children combined in the US have been diagnosed with epilepsy as of 2016 (1.6%). The total indirect and direct cost of epilepsy in the United States is estimated to be $15.5 billion annually. This estimate is based on a reported cost of $12.5 billion in 1995 converted to 2004 dollar value using Bureau of Labor Statistics data. Approximately 60% of new onset epilepsy cases respond to existing antiepileptic drugs (AEDs) but 40% are pharmaco-resistant, having seizures that cannot be fully controlled with available medical therapy or without unacceptable side effects. Thus, there are at least 25 million people world-wide for whom the development of more effective epilepsy treatment paradigms would be greatly beneficial.

One challenge in the field of epilepsy management is the process of detecting seizures. Electroencephalograms (EEGs) detect the brain's electrical activity, and have traditionally been used in the detection and classification of seizures in epilepsy patients. The flowing currents, or impulses, sent between activated brain cells are captured by EEG machines over a period of hours or days and documented in a variety of formats. When using EEG data for the detection and classification of epileptic seizures, the established practice has been to admit patients into long-term epilepsy monitoring units. During this time, epileptologists and trained technicians review EEG recordings over the course of many hours or days. By manually reviewing the patterns of activity in an EEG recording across many hours, or even days, epileptologists mark time points where a seizure is thought to have occurred.

As computational capability has increased, new signal processing methodologies have been developed in an attempt to analyze EEG data for the purpose of seizure detection. However, electrical noise and neuro-muscular artifacts introduced during the recording of EEGs can contaminate the true signal. This frequently has a negative influence in EEG signal processing, resulting in a decrease in the accuracy of seizure detection and classification, such as not detecting a seizure or indicating a false positive, and detection rate of seizure events widely inconsistent across different methods.

Inconsistencies in detection reporting also complicate the ability of successful real-time signal analysis, requiring a patient to sit for long periods, often without movement to avoid introducing artifacts, in order to successfully detect seizure events.

While numerous seizure detection methods exist, none are believed to show the detection of seizures with 100% sensitivity and 100% specificity. Other methods of seizure detection that do not involve neural measurements have been proposed, though they often have severe deficiencies. One such method implemented uses patient movement data collected by accelerometers during a seizure event; however, this method is ineffective since not all seizures manifest themselves clinically in outward behavioral changes. The consequences of poor seizure detection methods include a reduction in quality of life for the patient, longer hospital stays resulting in increased costs, other health complications, or mortality.

SUMMARY OF THE INVENTION

A system for detecting a seizure associated with a subject comprises a cap with a plurality of electroencephalogram electrodes that can be connected to a subject. An electroencephalogram machine is connected to the cap that records electroencephalogram data and a display device. A computer system in communication with the electroencephalogram recording machine is configured to receive electroencephalogram data. The system generates a set of Kantz algorithm parameters and process the electroencephalogram data associated with a subject. The set of Kantz algorithm parameters identify a series of Lyapunov exponents. The system determines the electroencephalogram data is associated with an epileptic seizure based upon the series of Lyapunov exponents. The system may cause the display device to display a representation of the series of Lyapunov exponents.

A computer-implemented method detects a seizure associated with a subject. The method is executed by one or more computer systems and comprises receiving electroencephalogram data associated with a subject, generating a set of Kantz algorithm parameters, and processing the electroencephalogram data associated with a subject. The set of Kantz algorithm parameters is used to identify a series of Lyapunov exponents. The method includes determining the electroencephalogram data is associated with an epileptic seizure based upon the series of Lyapunov exponents.

A computer-implemented method detects a seizure associated with a subject. The method is executed by one or more computer systems and comprises receiving electroencephalogram data derived from a subject who has been administered an electroencephalogram exam by way of electroencephalogram input devices attached to the subject. The method identifies an optimal set of Kantz algorithm parameters by iteratively evaluating possible values for each parameter using historical EEG data. The method processes the electroencephalogram data associated with a subject using the set of Kantz algorithm parameters to identify a series of Lyapunov exponents. The Lyapunov exponents are identified by plotting a log distance versus evolution time of the electroencephalogram data and determining a gradient of the plot of log distance versus evolution time. The method determines the electroencephalogram data is associated with an epileptic seizure based upon the series of Lyapunov exponents.

DETAILED DESCRIPTION OF THE INVENTION

Figure 1:
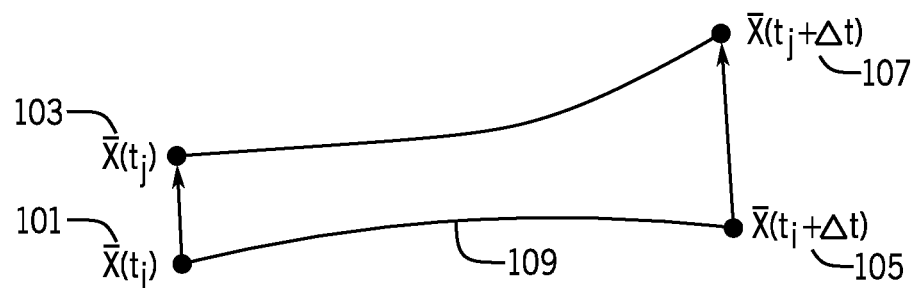
FIG. 1 is a diagram of a single evolution of a perturbed fiducial trajectory in time Δt.

The following claims are not meant to be limited to the particular embodiments and examples herein. The disclosed invention will be described by referencing the included figures illustrating preferred embodiments.

In typical EEG machines, signals are collected with electroencephalogram electrodes placed along the scalp, the number of which can vary. These electrodes measure voltage fluctuations of the neural tissue of the brain, comprising billions of individual neurons. Communication between neurons is facilitated through the exchange of ions through the cell membranes and the generation of action potentials, where a sudden release of ions can cause measurable changes in the electric potential between the inside of a neuron and the surrounding interstial space.

Rapid changes in electrical potential can propagate throughout the brain, interacting with other changes induced by ion movement in other cells. The brain can thus be thought of as a dynamic non-linear system of interacting ion currents and electric potentials without a steady state. The broad range of complex cognitive and neural processes that underlie everyday human activity creates difficulties in characterizing the non-linear dynamics for identifying functionally related features and system attractors. It has been shown that EEG data recorded in humans and animals are not just random stochastic signals as they were thought of in the past, rather they can be described as electrical activity generated by a chaotic oscillator that is a fundamental part of the brain's operating mechanism.

The chaoticity of a nonlinear oscillator, such as that characterized by captured EEG data, can be quantified by means of the oscillator's maximum Lyapunov exponent ($L_{max}$). Once calculated, the Lyapunov exponents, which may be used to characterize rates of separation in the EEG data, may be utilized, as described herein, by an EEG machine to more efficiently and accurately detect seizure events within an individual being monitored.

In the absence of state equations that describe a dynamical model of the brain, computing the Lyapunov exponent means relying on an established embedding theorem which allows a single observed variable to be expanded into a higher dimensional state-space. The Lyapunov exponent can then be computed as a mean logarithmic deviation of the trajectories in the higher dimensional space over time.

A first step in computing the Lyapunov exponent is to create a delayed vector of observed values from a time series. It has been shown that this delayed signal contains all the state variables of the system being observed. In the case of EEG data, this method can be used to reconstruct the multidimensional state space of the brain's electrical activity from each EEG channel. For example, if x(t) is a 1×n dimensional vector of duration T recorded from an EEG channel sampled every $T_s$ seconds, then $X_i(t)$ is the p dimension of embedded signal within x(t) such that $$\overline{X}_i(t)=[x(t_i), x(t_i+\tau), \ldots, x(t_i+(p-1)*\tau)]^T$$

where, τ is the delay between successive components of $\overline{X}_i(t)$ and it rarely, if ever, is the same as $T_s$. If a phase space plot of the p×n dimensional vector $\overline{X}_i(t)$ were to be created, then it would look like that of a strange chaotic attractor.

An attractor is defined as chaotic if the largest of all its Lyapunov exponents ($L_{max}$) is positive. The complexity of this attractor is measured by its dimension D, a quantitative characterization of complex geometrical phase-space of a system. It has been shown that for a sinusoidal attractor the value of D=1, and for that of a chaotic attractor such as those found in EEGs of epileptic patients, D is typically found to be between 2.5-2.7. A description of how D can be estimated from time series data via its state space correlation dimension ν has been recorded. The measure of chaoticity of these attractors can be defined via either their Kolmogorov Entropy or their Lyapunov exponents.

The method for choosing p, the embedding dimension of the state space of the signal x(t), may be p≥(2*D+1). Although the dimension of an attractor can be fractal, that of the embedded signal p, cannot. The brain is a non-stationary system and as such may not reach steady state; so its value for D is never constant. This is why, in some embodiments, a time window of T=10 seconds (or other values, such as 7 seconds or 12 seconds, or durations lasting less than 30 seconds) may be chosen so as to better satisfy the assumption of stationarity for the signal. An example value of p=7 may not be changed for signal analysis in the epoch before, during, or after (pre-ictal, inter-ictal, and post-ictal stages, respectively) a seizure is suspected. The justification is that the existence of irrelevant information in dimensions higher than 7 might not greatly influence the estimated dynamical measure. Furthermore, reconstruction of the state space with high p suffers more from the short length of moving windows that are used to handle non-stationary data.

$L_{max}$ may be estimated from stationary data using a Wolf algorithm that has been modified to compute the average short-term maximum Lyapuonv exponent ($STL_{max}$) for non-stationary EEG data on short time windows. $STL_{max}$ can be calculated using the Wolf algorithm as follows:

$$STL_{max} = \frac{1}{N_a \Delta t} \sum_{i=1}^{N_a} \log_2 \frac{|\delta \overline{X}_{i,j}(\Delta t)|}{|\delta \overline{X}_{i,j}(0)|}$$

where $\delta \overline{X}_{i,j}(0) = \overline{X}(t_i) - \overline{X}(t_j)$ is the displacement vector at time $t_i$, i.e., a perturbation of the fiducial orbit at $t_i$, and $\delta \overline{X}_{i,j}(0) = \overline{X}(t_i + \Delta t) - \overline{X}(t_j + \Delta t)$ is the evolution of this perturbation after time $\Delta t$. This is illustrated in FIG. 1. $\Delta t$ 109 (represented along a horizontal axis of FIG. 1) is the evolution time for $X(t_i)$ 101 and $X(t_j)$ 103 i.e. the time over which measured values evolve in the state space to $X(t_i + \Delta t)$ 105 and $X(t_j + \Delta t)$ 107. FIG. 1 therefore depicts a single evolution of perturbed fiducial trajectory in time wherein the final fiducial trajectory is associated with time $t_i$.

When the evolution time $\Delta t$ is given in seconds, $STL_{max}$, has units in bits/second. $N_a$ is the number of local Lyapunov exponents that are estimated within a duration time T of a data segment. This gives the following relation between T, the length of a segment of data, and $\Delta t$ the evolve time:

$T = (N-1)\Delta t \approx N_a \Delta t (p-1)\pi$

Other methods may be utilized to estimate the Lyapunov exponent. Wolf's algorithm, for example, in the reselection process after every evolution time $\Delta t$, selects a new candidate for the nearest neighbor to the fiducial trajectory. This process can, in some circumstances, lend itself to increased error in the presence of even the slightest amount of noise in the data, rendering the Wolf method less effective in cases with highly noisy data such as EEG data. One relatively new method for calculating Lyapunov exponents, the Rosenstein algorithm, is based upon the selection of an initial fiducial trajectory after the application of a prior embedding theorem. To reconstruct the state-space in higher dimensions, the average divergence between two points in the fiducial and its nearest neighbor trajectory d(t), at time t, is computed using the following equation, where C is a constant that normalizes the initial separation:

$d(t) = Ce^{Lmax t}$

In order to compute $L_{max}$ numerically, trajectories are allowed to evolve over the finite data set and a plot of log distance versus evolution time is generated. Then, the gradient of the initial part of the plotted log distance curve is $L_{max}$ for one trajectory pair. In this way for the rest of the data set, the process is repeated by moving forward one step at a time in the phase-space and computing an estimate for $L_{max}$. The average of all such $L_{max}$ values is the final result from the Rosenstein algorithm.

Another method for calculating Lyapunov exponents involves the Kantz algorithm. The Kantz algorithm also starts from computing the expanded phase-space trajectory. However, unlike the Rosenstein algorithm described above, instead of selecting a single nearest neighbor to track, the Kantz algorithm chooses a radius around the fiducial and computes the average of how all the trajectories within the radius separates from the fiducial. The log distance versus evolve time is plotted and like the Rosenstein algorithm, the gradient at the beginning of the plot is the value for $L_{max}$. This uses an exponentially greater number of trajectories and thus is more robust to perturbations in the signal, though inefficient implementations of the algorithm will make it too slow for any practical use in analyzing EEG data. It may be noted that in some embodiments the first few points in the evolution may be discarded if the maximal Lyapunov exponent at that time has not overtaken the other stable Lyapunov exponents.

Figure 2A:
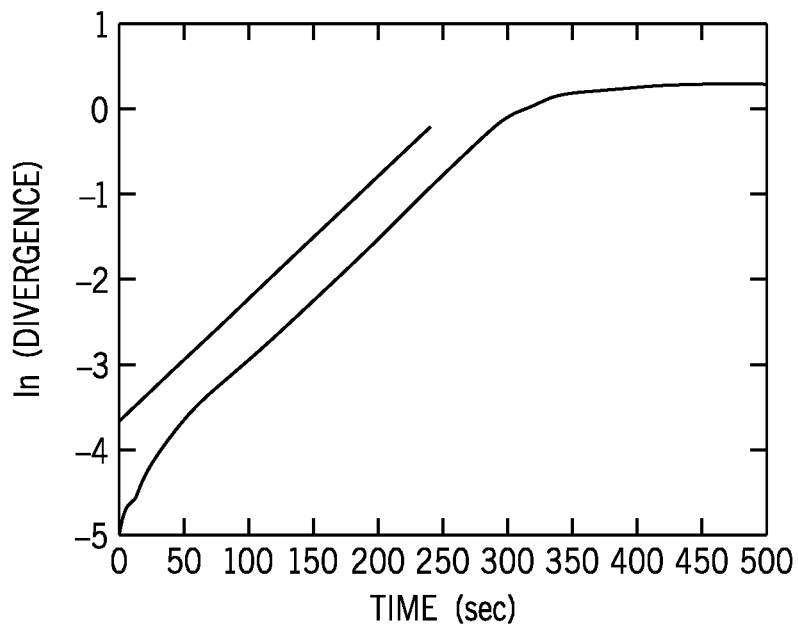
FIG. 2A depicts a data trace showing time on the horizontal axis vs log distance curves on the vertical axis of data depicting a Lorenz attractor sampled at 100 Hz processed using a Rosenstein algorithm.
Figure 2B:
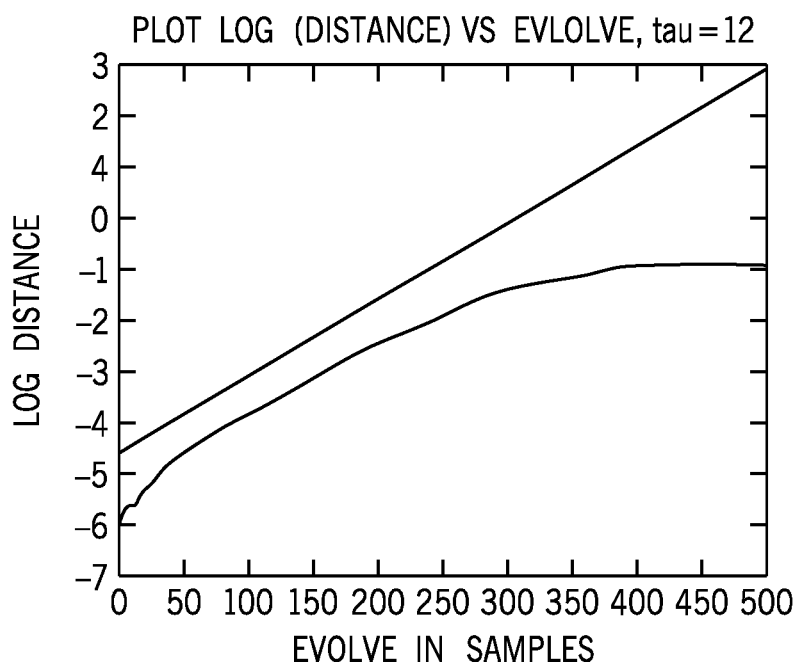
FIG. 2B depicts a data trace showing time on the horizontal axis vs log distance curves on the vertical axis of data depicting a Lorenz attractor sampled at 100 Hz processed using a Kantz algorithm.

These approaches, though each demonstrating different benefits and disadvantages can each be utilized to calculate Lyapunov exponents in complex data sets, such as those gathered when collected EEG data of a subject. To illustrate, FIGS. 2A and 2B show how these two methods are employed in computing $L_{max}$ for an example Lorenz attractor data set. In both FIGS. 2A and 2B the algorithms are applied to data sampled at 100 hz. FIG. 2A depicts application of the Rosenstein algorithm and FIG. 2B depicts the Kantz algorithm being applied to the same data set. The log distance curve in both cases was allowed to evolve for 500 samples. The straight line depicted in each of FIGS. 2A and 2B has a gradient that is the estimate of $L_{max}$. The Kantz algorithm (FIG. 2B) correctly estimates the value for $L_{max}$ at 1.487. The table below summarizes the values computed by all three methods for the Lorentz attractor using the same data.

| Method | Value | Error % |
| --- | --- | --- |
| Kantz | 1.487 | 0.867 |
| Rosenstein | 1.387 | 7.53 |
| Wolf | 1.3318 | 11.21 |
| Theoretical | 1.50 | N/A |

The Kantz algorithm can be implemented in this invention for improved detection of seizure activity and subsequent seizure classification using EEG recordings, as described herein.

Figure 3:
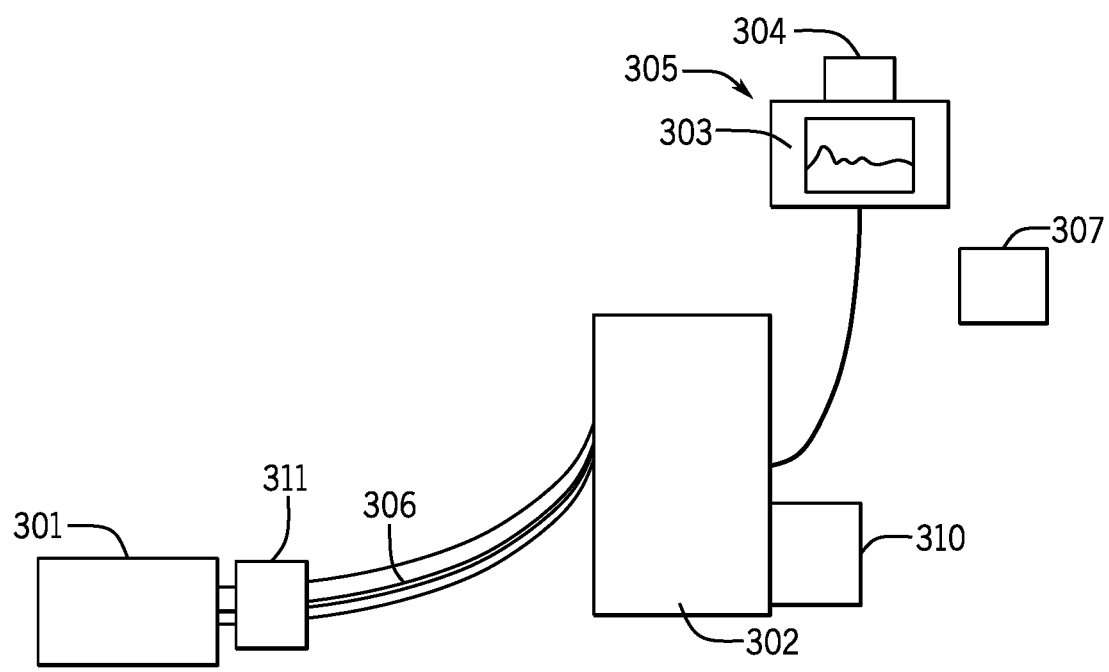
FIG. 3 depicts an environment in which the present system may be implemented including an EEG machine coupled to input sensor electrodes located in an EEG cap for subject monitoring in which the EEG machine is also connected to a computer system for output display of graphical representations of data obtained via the EEG cap.

FIG. 3 depicts an example embodiment a system configured in accordance with the present disclosure to detect seizure events in an individual. In this example embodiment, an EEG cap 301 is placed on the scalp of a patient. One skilled in the arts will recognize that typically the number of electrodes that record data may vary depending on the specific configuration of the EEG cap, and the invention described herein is not limited by, or contingent upon a specific number of electrodes.

The EEG electrodes of EEG cap 301 may be placed on the scalp in locations at the discretion of the physician or EEG specialist such that they are able to record the electric potential fluctuations in the brain as a continuous analog signal from each electrode channel.

Neural data from each electrode channel (e.g., each sensor or electrode of EEG cap 301) is transmitted through electrode wires 306 to EEG machine 302 where the data is recorded as a data stream for each channel and stored in a memory array. The EEG machine may be any clinical unit or other device with sufficient processing power and a means to record electrical potential. In some embodiments the continuous analog signal from each electrode channel may be recorded and transmitted as individual temporal data segments; for example, the full duration of a recording session may be recorded and transmitted in 10 second epochs, though other epoch lengths may be used as well. In some embodiments, external sensors 311 connected to the electrode wires may separate the data epoch transmissions by a finite amount of time, for example, 2 seconds, in order to record a non-continuous set of EEG data epochs. EEG machine 302 may include a controller 310 configured to control the temporal parameters of data collection from EEG cap 301, such as the length of data epochs and the sensors 311 controlling time between epochs.

In some embodiments, the EEG machine 302 may be connected to a computer system 305 or other processor configured to process the recorded signal data. Computer system 305 can combine individual data epochs from a plurality of EEG electrode channels to generate a composite data set for EEG data for a given window in time.

In various embodiments, computer system 305 may utilize an operational data processing pathway configured to calculate the individual Lyapunov exponents for each composite EEG data set using an optimized Kantz algorithm, as described above.

In some embodiments, to facilitate data processing a controller in the computer system 305 may increase the signal-to-noise ratio of the $L_{max}$ data set to some degree by averaging the individual Lyapunov exponents for a composite data set. In some embodiments, there may be additional data processing such as filtering. For example, a Butterworth linear filter of sufficiently high order may be used to reduce noise without distorting the data itself. Other similar linear or nonlinear measures may also be implemented. In some embodiments, the computer system 305 may be configured to display the averaged Lyapunov exponents calculated over a time window on an EEG display screen 303 in real-time. This may enable real-time monitoring of the EEG neural activity by a physician or other specialist for seizure related activity.

In still other cases, computer system 305 may be configured to use pattern recognition to assist in epileptic seizure detection. In some embodiments this may include autonomous, semi-autonomous, or passive assistance. A database 307 of EEG data patterns that correspond to pre-ictal, inter-ictal, or post-ictal seizure events may be stored in computer system 305 or other memory array 304. The computer system 305 may be configured to compare EEG activity pattern profiles stored in the database in to the real-time EEG data streams to detect an epileptic seizure in the ongoing composite EEG data stream.

In some embodiments, the computer system 305 may use the Kantz algorithm to allow for better estimation of the Lyapunov exponent and provide more accurate and time-efficient detection of seizure events. The Kantz algorithm has many more tunable parameters than prior existing methods, providing a better method of detection. Extensive research has produced an optimization scheme for Kantz algorithm parameter values to show the maximum separation between the $L_{max}$ values for this method. Typically, a computer or other machine with sufficient computational power may analyze EEG data recorded from a subject to optimize the parameter selection that provides maximum detection capability. A plurality of Kantz algorithm parameters are systematically tested for optimization. Using an EEG data set known to contain seizure activity, one parameter is systematically tested with a range of values while other parameter values are kept static. Each parameter in the algorithm is then tested until an optimum Lyapunov profile for the known seizure data is achieved. For example, a typical parameter search may entail computing Lyapunov profiles with 1000 or more different permutations of parameter values until an optimal parameter set is found that shows the clear changes in preictal, ictal, and postictal $L_{max}$ values typical of a seizure. In some embodiments, parameter sets may be used for multiple subjects or seizure types. In other embodiments, the parameters may be retuned for more accurate seizure detection.

Typically, the use of 100 or 1000 times more information in the Kantz algorithm could lead to processing becoming computationally expensive. However, with a proper selection of parameters and efficient utilization of computer system 305 as described herein, the computations can be performed in real-time.

The use of the optimized Kantz algorithm offers distinct advantages over the use of existing detection paradigms. The Lyapunov profile in an epileptic patient shows a very distinct pattern during seizure that becomes apparent over time utilizing the system and methods as described herein. This pattern may not be discernible, and at times absent, while using existing methods. The presence of a distinct Lyapunov profile pattern during seizure enables the computer system 305 or other processing component to implement a pattern recognition protocol. This pattern recognition protocol uses a threshold to detect a seizure by using an average of the $L_{max}$ values from all channels of EEG for each data epoch. In other embodiments, pattern recognition may be accomplished by analyzing features using artificial neural network computing systems.

Thus seizure detection may be fully automated in some embodiments, removing the possibility of human error and reducing the need for extended time periods of data collection. In the past it had been standard for EEG data to be recorded and manually monitored for hours or days to detect the occurrence of a seizure. The present system and method provide a means to more efficiently and accurately detect seizure activity patterns than conventional approaches.

In some cases, it may be important for physicians or other specialists to conduct a post-hoc review of the recorded EEG data. Accordingly, some embodiments of the present system may enable offline computation and analysis of the Lyapunov exponents of EEG data. In that case, EEG cap 301 may transmit data to EEG machine 302 during real-time recording. EEG machine 302 may collect, for example, 10 second epochs (though epochs may have other durations such as 8 or 12 seconds) of EEG data from a subject via a plurality of electrode channels in EEG cap 301. For typical human subjects, EEG data may be recorded on 16-128 EEG channels. In general, a higher number of channels may have greater spatial specificity of the location of seizure activity within the brain. In some embodiments, a greater number of channels may improve the ability to reduce noise in the signal and improve the clarity of the $L_{max}$ values. Epochs of neural data from each EEG channel may be transmitted by the EEG machine 302 to a memory array on computer system 305 or another component with suitable data storage capabilities. The systems and methods of seizures detection may then be used for analysis of the data at a later time. In this example, the optimized Kantz algorithm may be applied to each previously recorded 10 second epoch of data across all electrode channels for a specific window of time. This process may be repeated for all recorded data by moving the analysis window forward in time by a certain amount of time, e.g.: 2 seconds, until a computation of $L_{max}$ for the entire EEG data set is completed. Seizure related events may then be detected and classified post-hoc.

Figure 4:
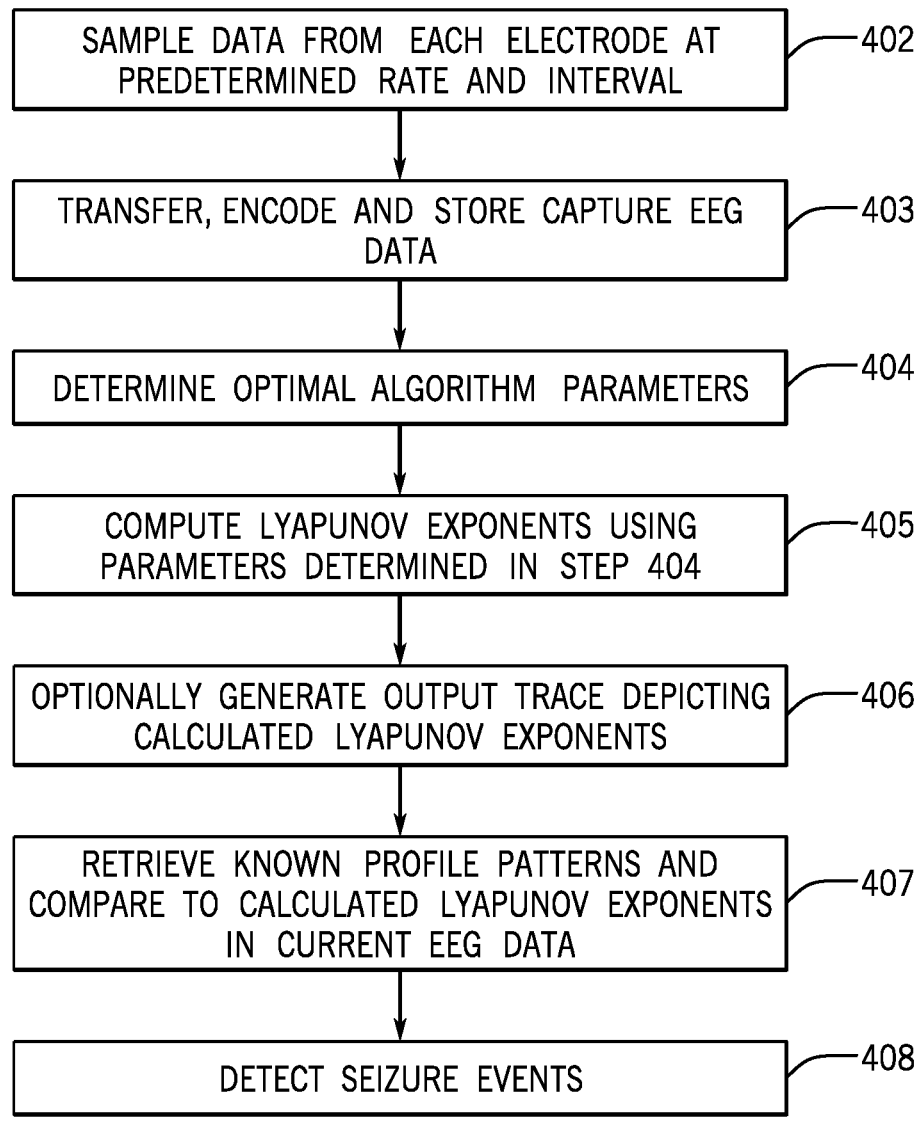
FIG. 4 is a flow chart depicting an example method for detecting a seizure event in accordance with the present disclosure.

FIG. 4 is an example flow chart describing the steps of detecting a seizure using the methods described herein. The method depicted in FIG. 4, for example, may be implemented by the system depicted in FIG. 3 and, specifically, steps of the method may be performed by EEG machine 302 and computer system 305.

In step 401 EEG data is recorded from neural activity as an analog signal, using, for example, the EEG cap 301 as depicted in the FIG. 3. In step 402 of the method, an EEG machine (e.g., EEG machine 302) samples the data at a specified rate and interval to create data epochs, each epoch consisting of an EEG signal for each channel recorded over discrete time periods separated by a discrete length of time. The sampled data from an EEG machine is then transferred to a computer, processor, or memory array, as illustrated in step 403, where it can be further processed.

Using the parameter optimization scheme described, in step 404 the optimal parameters of the Kantz algorithm are computed for each channel of EEG data. In step 405, with the algorithm parameters optimized, the optimized Kantz algorithm is used to compute the Lyapunov exponents for each data epoch, creating measure of the chaoticity of the EEG activity for different electrodes at each data epoch. As described above, in some embodiments, this may involve plotting a log distance versus evolution time of the captured EEG data and determining a gradient of the plot of log distance versus evolution time.

In some embodiments, in optional step 406 the computer or processor may display the Lyapunov exponents on a display device, providing healthcare or research professionals with visual feedback of the chaoticity of ongoing neural activity.

In step 407, the computer compares the Lyapunov exponents of the ongoing activity to known patterns of seizure activity using a pattern recognition paradigm. This may involve, for example, the computer retrieving from a database, a plurality of historical Lyapunov exponents associated with seizure activity.

In step 408 a seizure may be detected when the Lyapunov exponents profiles of the ongoing EEG activity matches the profile of historical Lyapunov exponents associated with known seizure activity.

Figure 5:
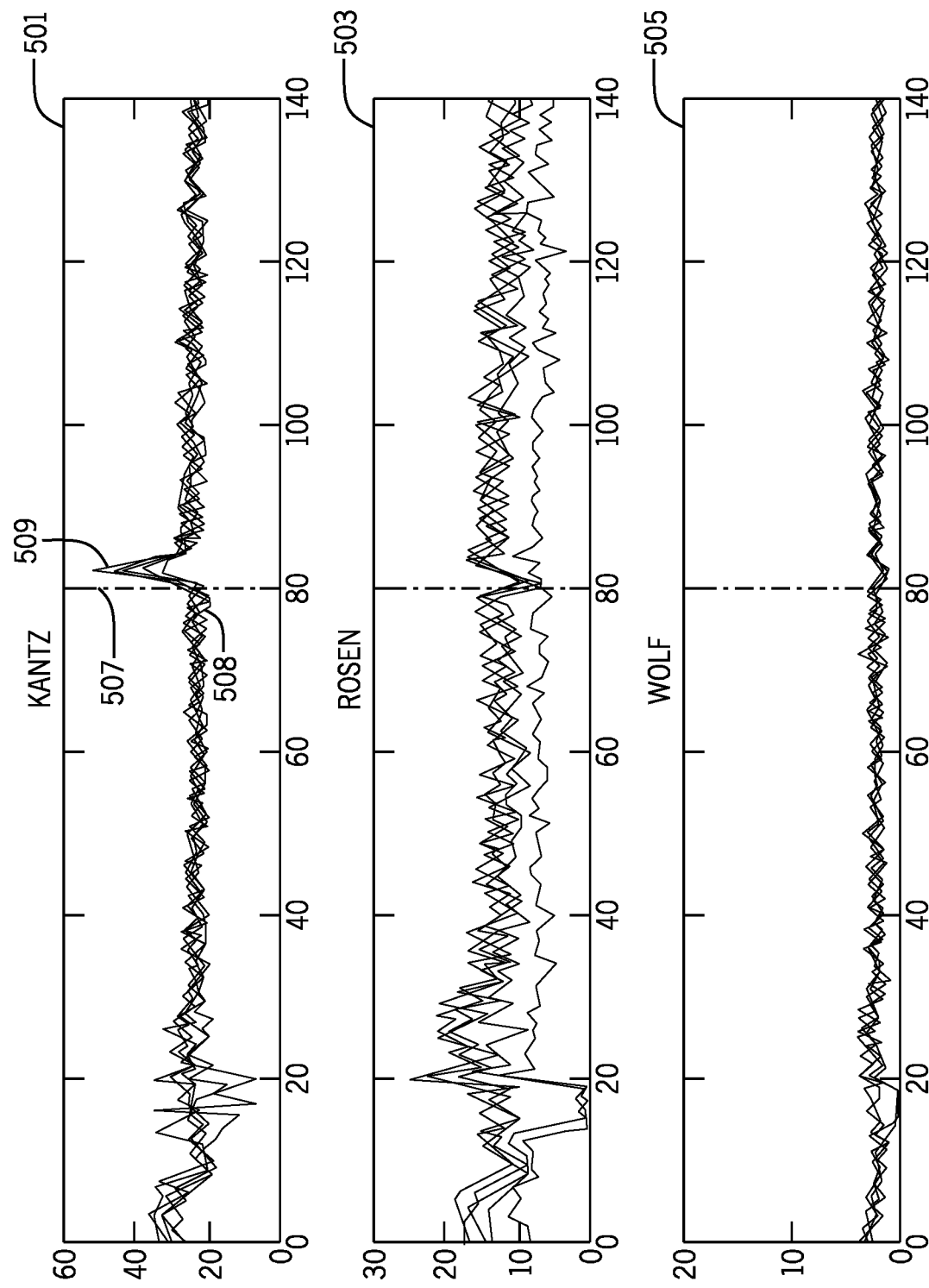
FIG. 5 shows a number of data traces depicting comparisons of $L_{max}$ values computed from data analyzed using Kantz, Rosenstein, and Wolf methods.

FIG. 5 shows a number of traces depicted the comparison of $L_{max}$ computed from the system and method described herein 501, as well as two existing methods 503 and 505. In this example, a seizure starts at the 80th time point represented by line 507. For the $L_{max}$ values of 501, the seizure can be clearly seen by the slight drop 508 and subsequent sharp increase 509 in magnitude of the $L_{max}$ plot. The Rosen method of 503, by comparison, is noticeably noisier and provides less robust detection. The Wolf method of 505 has very low magnitude values and an ambiguous response around the seizure event at the 80th time point 507. In some cases, the Wolf and Rosenstein algorithms may show a drop in the Lyapunov exponent values, but this is not consistent from seizure to seizure and thus will produce false negatives. In addition to real-time implementation capabilities, using the Kantz algorithm 501 with specific tuning parameters for system components provides the best possible feature for detection.

Figure 6:
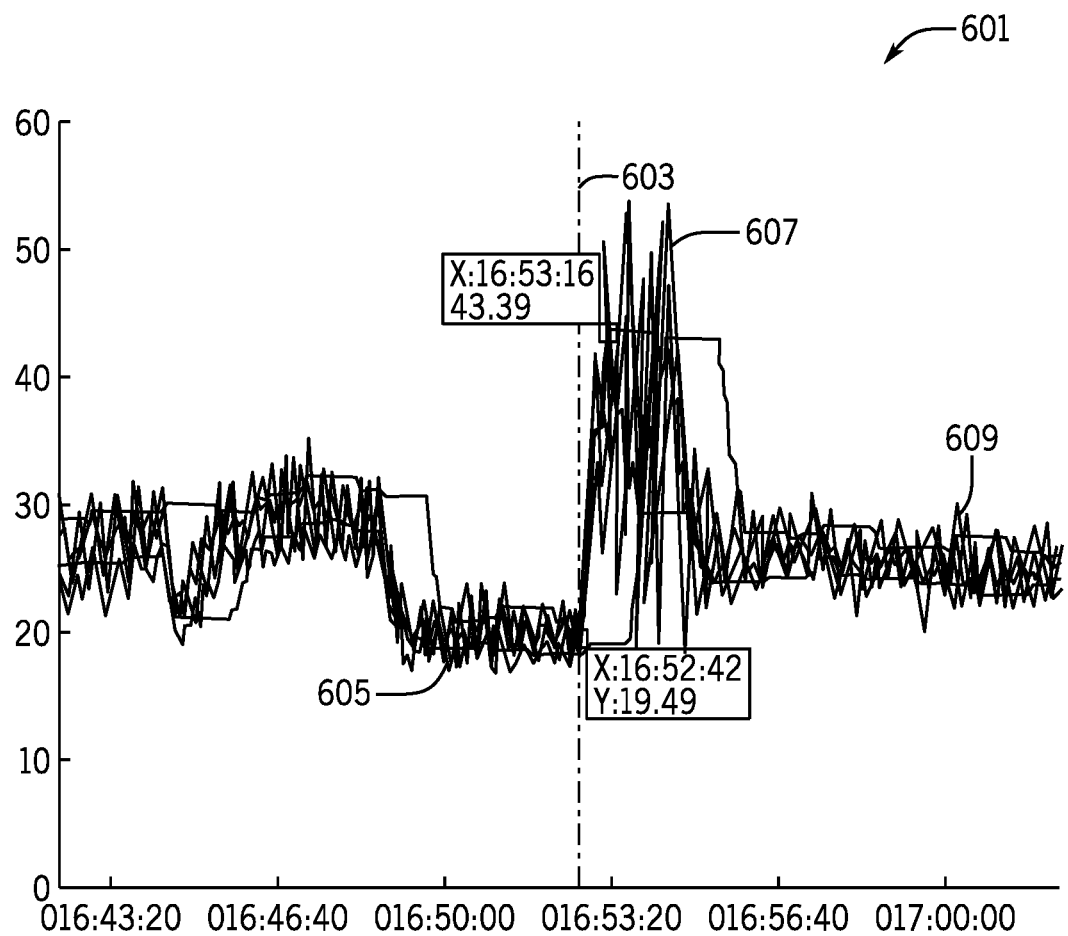
FIG. 6 shows a data trace depicting $L_{max}$ values computed using an optimized Kantz algorithm on EEG data of a subject.

FIG. 6 is a graph 601 showing the $L_{max}$ values on the y-axis and time on the x-axis. Compared to the Kantz graph 501 of FIG. 5, graph 601 is on a much smaller timescale, and therefore has greater temporal resolution which more clearly shows how $L_{max}$ values change around a seizure event. Here, graph 601 shows the $L_{max}$ values that were computed by the optimized Kantz algorithm from EEG data recorded in an animal subject around the time of a seizure. As illustrated in FIG. 6, a seizure starts at approximately 16:52:52 as indicated by vertical line 603. As can be seen, the magnitude of the Lyapunov exponents abruptly drops below the mean value in the time period 605 occurring just before the seizure. When the seizure occurs at time 603, the Lyapunov exponents rise to peak 607 much higher value than its mean value, before eventually dropping back to the level before the seizure started during time period 609. To detect a seizure, the Lyapunov exponents profile of rising and falling $L_{max}$ values during ongoing EEG activity depicted in FIG. 6 may be matched to a profile of historical Lyapunov exponents associated with known seizure activity. Looking at FIG. 6, the Lyapunov exponents profile is comprised of the $L_{max}$ values a few moments before and after the seizure occurred, indicated by line 603. When the pattern of $L_{max}$ values matches a similar pattern in a historical database, a seizure is detected. In some embodiments a threshold based detection method may be used. In this method, the criteria for seizure detection is the rate at which the $L_{max}$ values change as they decrease from the mean value to a lower value 605 and increase to peak 607 before returning to the mean value as in 609. Each threshold can be adjusted from subject to subject to improved detection according to receiver-operator characteristics, explained further below. Typically threshold values allow the changes in values to be detected before, during, and after a seizure.

Figure 7:
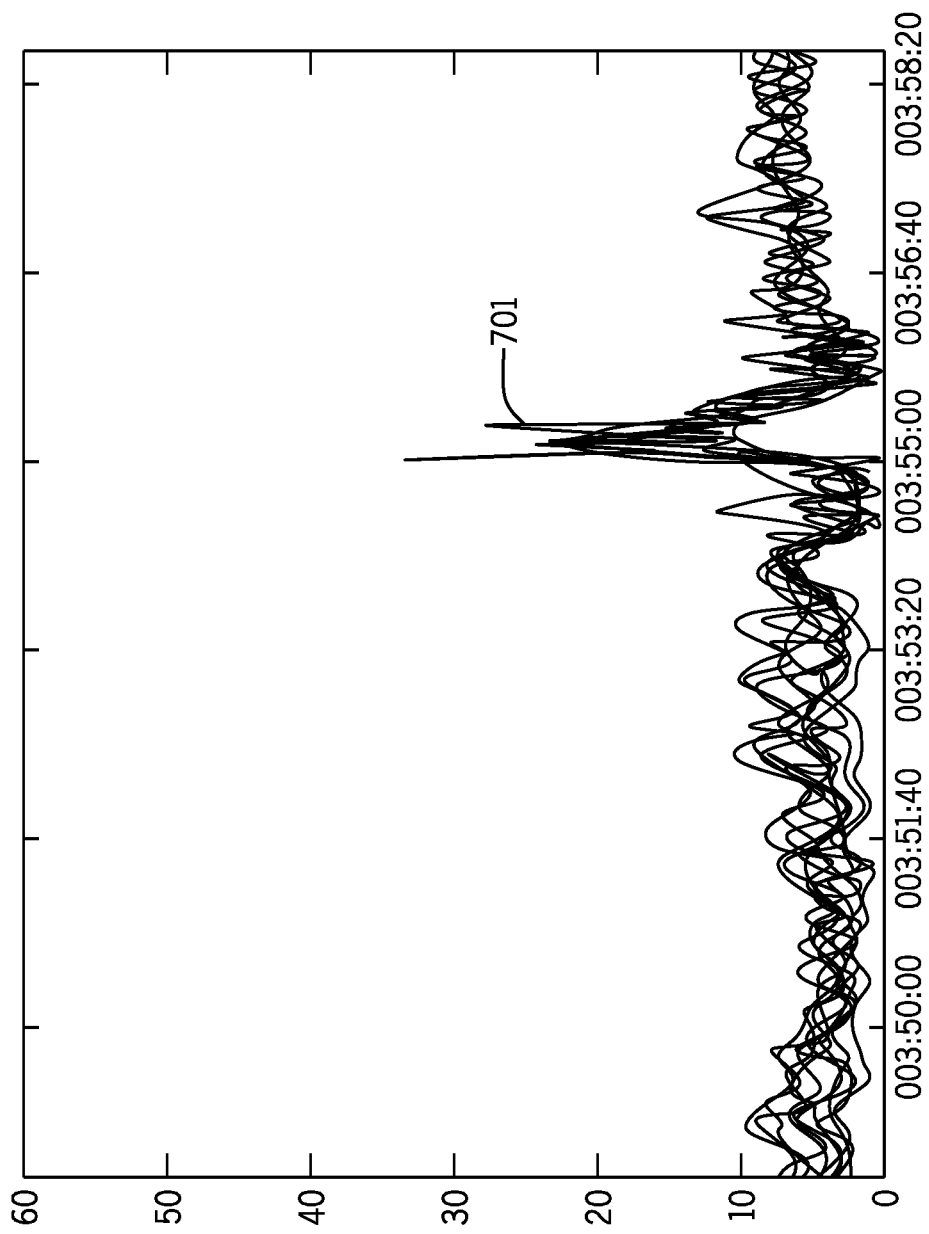
FIG. 7 shows a data trace depicting $L_{max}$ values computed using an optimized Kantz algorithm on EEG data of a subject.

FIG. 7 shows the same method on human data, with a seizure being detected by the increase in Lyapunov exponents depicted at point 701.

Figure 8:
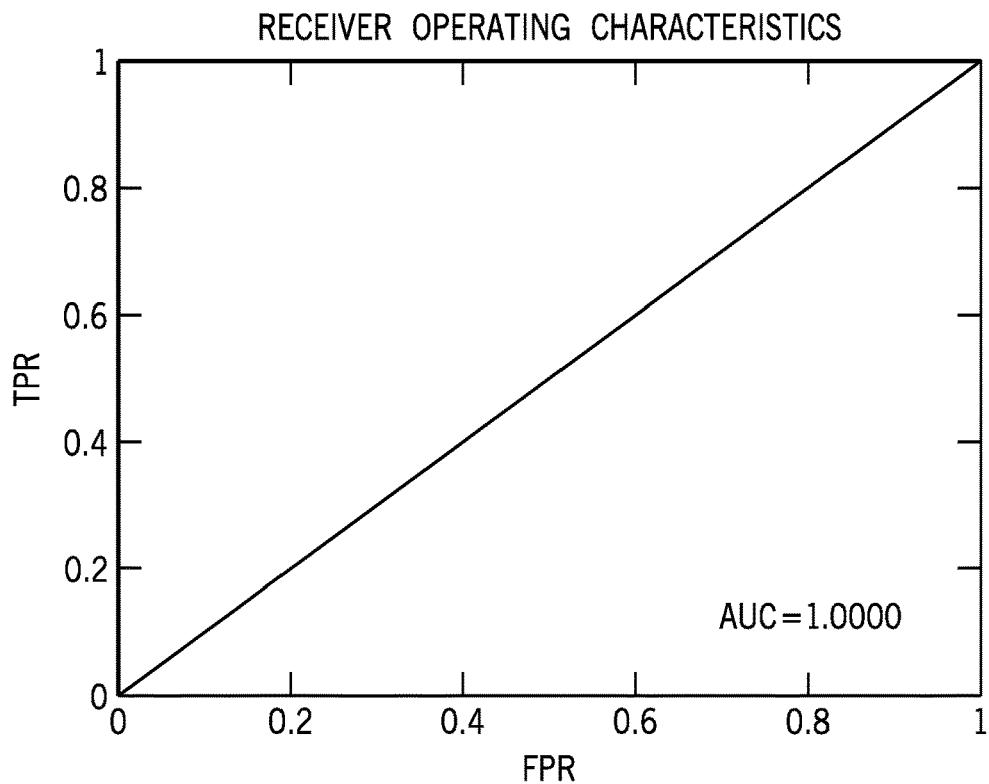
FIG. 8 shows a receiver-operator-characteristic (ROC) curve for a subject.
Figure 9:
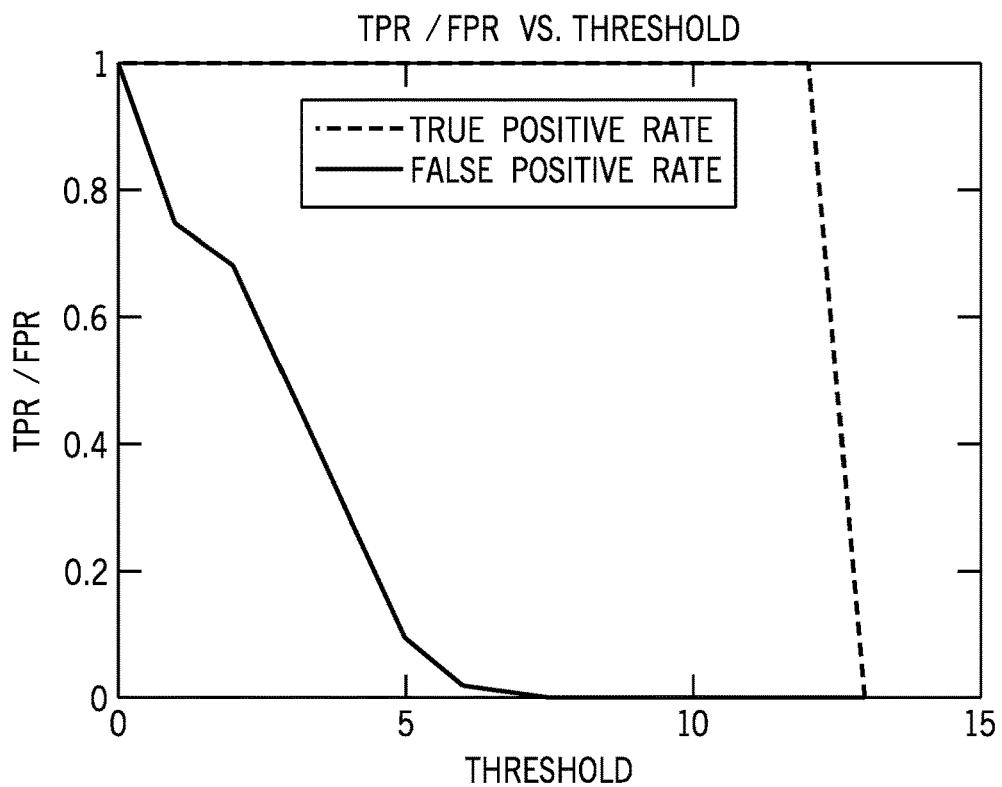
FIG. 9 shows how the detection threshold affects the ROC curve.
Figure 10:
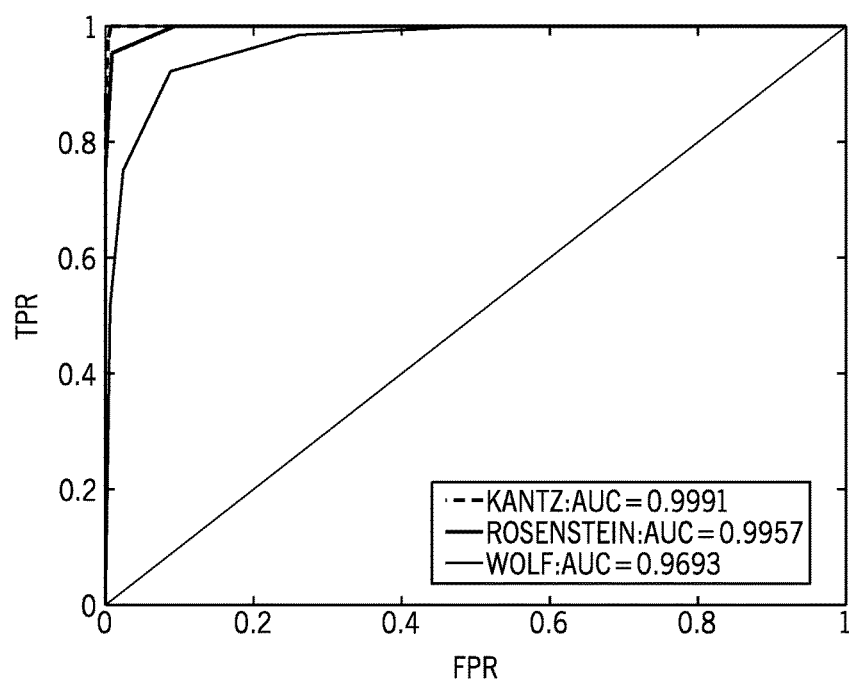
FIG. 10 shows a comparison of ROC curves for three detection methods.

In all seizures studied, including thousands of hours of EEG recorded from multiple different animals and a human patient, the activity pattern (such as the patterns depicted in FIGS. 6 and 7) is distinctly visible and detectable by the optimized parameter system and method described here. In some embodiments, the detection process may be automated using a thresholding algorithm based on an average of the $L_{max}$ computed for EEG neural data recorded and transmitted from all electrode channels used to record a subject. The threshold for detection may be manipulated to achieve 100% sensitivity and 100% specificity. Referring to FIG. 3, in one embodiment, a controller on the computer system 305 may be used to change the setting of the threshold, though in alternative embodiments this controller may be included in EEG machine 302 or EEG machine controller 310 or other suitable device. The threshold may be manipulated to compensate for such things as high noise levels in the signal or movement-related artifacts. For one example, there may be EEG recordings from an animal where the signal contains too much noise. In this example, the threshold can be manipulated to allow the sensitivity and specificity levels drop to compensate for the poor signal quality. FIG. 8 illustrates these results through the use of Receiver-Operator-Characteristics (ROC) curves. The true positive rate (TPR) is plotted on the y-axis, and the false positive rate (FPR) is plotted on the x-axis. In this example, the area under the curve (AUC) is 1.00, implying 100% sensitivity and specificity. FIG. 9 illustrates the relationship between the threshold and ROC curves. The figure shows how the (TPR) and (FPR) varies as the threshold is changed. As can be seen in the figure, there is an optimized value for the threshold where FPR=0.00 and TPR=1.00. When fully optimized in any classification algorithm, the algorithm will have 100% sensitivity and 100% specificity. However, the presence of noise and artifacts in the data can cause the area under the curve be less than 1.00 despite optimizing threshold value. Detection paradigms used in prior art, specifically the Rosenstein and Wolf algorithms, will always yield a worse AUC than the Kantz algorithm. For example, FIG. 10 is a figure illustrating the AUC for three different detection algorithms for a noisy EEG data set. Here the ROC curve and their AUC are presented for the Kantz, Rosenstein, and Wolf detection methods.

In FIG. 10 the TPR/FPR vs Threshold curve for the all three methods on the same noisy EEG data set. As can be seen all algorithms can have TPR=1.00 for certain thresholds, but the Kantz has lower FPR than the others at all points, demonstrating that the modified algorithm described herein performs better than other existing ones in identifying seizures. The automated detection algorithm can compare pattern profiles of known seizure events stored in a database such as database 307 of FIG. 3 to the pattern of Lyapunov exponents in an ongoing real-time data or previous recordings. The algorithm is also capable of distinguishing Lyapunov profiles from non-seizure epochs, preventing false positives.

In one example, the Wolf algorithm of a previous method indicated the occurrence of a seizure via a characteristic drop and rise in the Lyapunov exponents. When the system and methods described herein that employ the optimized Kantz algorithm were applied to the same data no sign of a seizure was detected. Additionally, a data set that was marked as a seizure by a technician was examined. Upon application of the invention of the current disclosure, no seizure was observed. Upon further professional review of that EEG signal by a trained specialist, the conclusion was that a seizure did not manifest itself, confirming the result of the present automated detection device.

Although the subject matter has been described in language specific to structural features and/or methodological acts, it is to be understood that the subject matter defined in the appended claims is not necessarily limited to the specific features or acts described. Rather, the specific features and acts are disclosed as illustrative forms of implementing the claims.

One skilled in the art will realize that a virtually unlimited number of variations to the above descriptions are possible, and that the examples and the accompanying figures are merely to illustrate one or more examples of implementations.

It will be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular embodiments disclosed, but that such claimed subject matter may also include all embodiments falling within the scope of the appended claims, and equivalents thereof.

In the detailed description above, numerous specific details are set forth to provide a thorough understanding of claimed subject matter. However, it will be understood by those skilled in the art that claimed subject matter may be practiced without these specific details. In other instances, methods, apparatuses, or systems that would be known by one of ordinary skill have not been described in detail so as not to obscure claimed subject matter.

Reference throughout this specification to "one embodiment" or "an embodiment" may mean that a particular feature, structure, or characteristic described in connection with a particular embodiment may be included in at least one embodiment of claimed subject matter. Thus, appearances of the phrase "in one embodiment" or "an embodiment" in various places throughout this specification is not necessarily intended to refer to the same embodiment or to any one particular embodiment described. Furthermore, it is to be understood that particular features, structures, or characteristics described may be combined in various ways in one or more embodiments. In general, of course, these and other issues may vary with the particular context of usage. Therefore, the particular context of the description or the usage of these terms may provide helpful guidance regarding inferences to be drawn for that context.

What is claimed is:

1. A system for detecting a seizure associated with a subject, the system comprising:
   a cap with a plurality of electroencephalogram electrodes configured to connect to a subject;
   an electroencephalogram machine connected to the cap that records electroencephalogram data using the electroencephalogram electrodes;
   a display device; and
   a computer system in communication with the electroencephalogram recording machine, the computer system being configured to:
      receive, from the electroencephalogram machine, electroencephalogram data;
      identify a set of Kantz algorithm parameters by iteratively evaluating possible values for each parameter using historical electroencephalogram data;
      process the electroencephalogram data associated with a subject using the set of Kantz algorithm parameters to identify a series of Lyapunov exponents;
      determine the electroencephalogram data is associated with an epileptic seizure based upon the series of Lyapunov exponents; and
      cause the display device to display a representation of the series of Lyapunov exponents.

2. The system of claim 1, wherein the electroencephalogram data includes at least one data sample acquired over a discrete time.

3. The system of claim 1, further comprising a database that stores a plurality of historical Lyapunov exponents associated with seizure activity and wherein the computer system determines the electroencephalogram data is associated with the epileptic seizure based upon the series of Lyapunov exponents by comparing the series of Lyapunov exponents generated from the electroencephalogram data to the plurality of historical Lyapunov exponents associated with seizure activity stored in the database.

4. The system of claim 1, wherein the computer system processes the electroencephalogram data associated with the subject using the set of Kantz algorithm parameters to identify the series of Lyapunov exponents by:
   plotting a log distance versus evolution time of the electroencephalogram data; and
   determining a gradient of the plot of log distance versus evolution time.

5. The system of claim 1, wherein the electroencephalogram data is derived from the cap with the plurality of electroencephalogram electrodes configured to connect to the subject who has been administered an electroencephalogram exam.

6. The system of claim 1, wherein the computer system is further configured to:
   iteratively evaluate at least 1,000 different permutations of Kantz algorithm parameters by computing Lyapunov exponents using each permutation of Kantz algorithm parameters and the historical electroencephalogram data until an optimal set of Kantz algorithm parameters is identified, wherein the set of Kantz algorithm parameters is the optimal set of Kantz algorithm parameters.

7. The system of claim 1, wherein the computer system determines the electroencephalogram data is associated with an epileptic seizure by:
- computing a rate of change of the series of Lyapunov exponents;
- comparing the rate of change of the series of Lyapunov exponents to a predetermined threshold; and
- detecting the epileptic seizure when the rate of change exceeds the threshold.

8. The system of claim 1, wherein the computer system is configured to generate a rendering of the series of Lyapunov exponents identified from electroencephalogram data associated with a subject using the set of Kantz algorithm parameters, wherein the rendering of the series of Lyapunov exponents comprises a plurality of Lyapunov exponents rendered as a time series, wherein the epileptic seizure corresponds to a particular time of the time series.

* * * * *